(12) United States Patent
Decoux et al.

(10) Patent No.: US 11,229,470 B2
(45) Date of Patent: Jan. 25, 2022

(54) ENDOSTEAL GUIDE PIN, POSITIONING TROCAR AND TROCAR FOR REMOVING SAID PIN

(71) Applicant: HIRONDELLE MEDICAL, Aubagne (FR)

(72) Inventors: Eric Decoux, Saint-Gély-du-Fesc (FR); Nguyen-Thanh Denis Hoa, Saint-Gély-du-Fesc (FR)

(73) Assignee: HIRONDELLE MEDICAL, Aubagne (FR)

( * ) Notice: Subject to any disclaimer, the term of this patent is extended or adjusted under 35 U.S.C. 154(b) by 181 days.

(21) Appl. No.: 16/489,491

(22) PCT Filed: Mar. 15, 2018

(86) PCT No.: PCT/FR2018/050624
§ 371 (c)(1),
(2) Date: Aug. 28, 2019

(87) PCT Pub. No.: WO2018/167435
PCT Pub. Date: Sep. 20, 2018

(65) Prior Publication Data
US 2020/0085481 A1    Mar. 19, 2020

(30) Foreign Application Priority Data

Mar. 15, 2017 (WO) .................. PCT/FR2017/050595

(51) Int. Cl.
*A61B 17/58* (2006.01)
*A61B 17/60* (2006.01)
(Continued)

(52) U.S. Cl.
CPC ...... *A61B 17/8897* (2013.01); *A61B 17/3421* (2013.01); *A61B 17/3468* (2013.01);
(Continued)

(58) Field of Classification Search
CPC combination set(s) only.
See application file for complete search history.

(56) References Cited

U.S. PATENT DOCUMENTS

| 5,456,267 A | 10/1995 | Stark |
| 2004/0092936 A1 | 5/2004 | Miller et al. |

(Continued)

FOREIGN PATENT DOCUMENTS

| WO | 2009/091616 A2 | 7/2009 |
| WO | 2016/114769 A1 | 7/2016 |

OTHER PUBLICATIONS

International Search Report dated Sep. 5, 2018 in corresponding International application No. PCT/FR2018/050624; 6 pages.

*Primary Examiner* — Sameh R Boles
(74) *Attorney, Agent, or Firm* — Maier & Maier, PLLC (57) ABSTRACT

An endosteal guide pin for preparing a guide path for the implantation of a pedicle or orthopaedic screw into a patient's bone. The pin has a head intended to be provisionally implanted in a bone and a guide rod, coaxial with and rigidly secured to the head, ending in a free end intended to be at least level with the skin surface of the patient when the pin is in the implanted position in the bone. The pin has a first coupling part intended at least to secure the pin to and release the pin from at least one portion of a positioning trocar and a second coupling part intended at least to secure the pin to a removal trocar. Also, a trocar for positioning a guide pin, which trocar incorporates the guide pin, and to a trocar for removing the pin.

18 Claims, 7 Drawing Sheets

(51) Int. Cl.
*A61F 2/00* (2006.01)
*A61B 17/88* (2006.01)
*A61B 17/34* (2006.01)
*A61B 17/70* (2006.01)
*A61B 17/00* (2006.01)

(52) U.S. Cl.
CPC ...... *A61B 17/3472* (2013.01); *A61B 17/7091* (2013.01); *A61B 17/7001* (2013.01); *A61B 2017/0046* (2013.01)

(56) References Cited

U.S. PATENT DOCUMENTS

| | | | |
|---|---|---|---|
| 2009/0187194 A1* | 7/2009 | Hamada | A61B 17/8897 606/104 |
| 2010/0280558 A1 | 11/2010 | Biyani et al. | |
| 2016/0242792 A1 | 8/2016 | Sasing et al. | |

* cited by examiner

ENDOSTEAL GUIDE PIN, POSITIONING TROCAR AND TROCAR FOR REMOVING SAID PIN

FILED

The invention relates to the field of orthopaedic surgery and more particularly to the field of pedicle or orthopaedic screw implantation.

BACKGROUND

The implantation of pedicle screws in vertebrae is widely used in orthopaedic surgery, in particular to hold vertebrae in place and/or to stabilise fracture-type lesions. This technique is also referred to as pedicle screw spinal osteosynthesis.

Surgeries in this field have shown a recent evolution towards techniques that are less invasive than total exposure of the operating field. These new so-called minimally invasive surgeries prevent blood loss and tissue lesions, and reduce the time under anaesthesia and risks of infection. Although these minimally invasive techniques require the production of tools adapted for a smaller cutaneous opening, the correct positioning of the pedicle screw and the absence of any neurological lesion must also be ensured. To achieve this, the surgery is coupled with image guidance of the fluoroscopic, CT or MRI type for example, accompanying the guiding of the precise positioning of the pedicle screw.

The patent document WO2009091616 discloses a surgical tool for placing a provisional guide pin used to guide the implantation of the definitive pedicle screws. The surgery can be performed on a patient in the laid back position on an imaging table, and under radiological guidance, for example X-ray guidance. The tool primarily includes a positioning trocar at the end whereof a provisional guide pin is coaxially mounted such that it can be removed. A fixing rod is also mounted inside the positioning trocar and the guide pin. This fixing rod includes a sharp tip which, by projecting from the guide pin, allows said pin to be inserted. A sleeve equipped with a handle is also provided around the fixing rod and the positioning trocar. This tool enables the surgery to be performed in two stages.

Firstly, the guide pin is inserted into the vertebra by means of the tool and more particularly thanks to the capacity to remove the pin from the rest of the tool, which enables the guide pin to be disengaged from the opposite end of the tool. The pin is thus the only element to remain in the vertebra and can be removed when positioning the screws. The pedicle screw is thus fixed in the vertebra at the orifice previously prepared by the provisional guide pin.

The instrument described in this publication has a certain number of drawbacks. Firstly, this instrument is complex as a result of the number of parts involved, which can generate difficulties in ensuring the maintenance of the guide pin in the screwed vertebra and which creates risks of infection and excessively long surgery durations.

Moreover, the high number of manipulations as a result of the number of parts involved in this tool requires a sufficiently large surgical space. However, the configuration of this instrument requires the surgery, in its entirety, to be carried out with image guidance to ensure the insertion of the guide pin, the removal thereof, and the insertion and fixation of the pedicle screw. This results in a need for a large amount of space in a limited working space, for example a CT scanner.

Finally, the complexity of the tool increases the manufacturing cost thereof.

SUMMARY

The invention relates to an instrument formed by a provisional guide pin and parts for inserting and removing this pin, which ensure the easy placement of the guide pin as well as the subsequent placement of the pedicle screw, without being confronted with the aforementioned problems.

In particular, the invention relates to an instrument which comprehensively provides improved precision and safety for the patient, without being subjected to the aforementioned spatial requirement issues.

The invention further relates to a simple instrument for a reduced manufacturing cost.

Finally, the invention relates to an instrument that is capable of being adapted to a method for implanting pedicle or orthopaedic screws, wherein the operations for placing the guide pin and for placing the pedicle screw can be separated.

The invention relates to the use of an endosteal guide pin for preparing a guide path for the implantation of a pedicle or orthopaedic screw, which pin is essentially characterised in that it includes a head intended to be provisionally implanted in a bone, and a guide rod, coaxial with and rigidly connected to the head, ending in a free end adapted such that it is at least flush with the skin surface of the patient when the pin is in the implanted position in the bone, which pin includes a first coupling means intended at least to ensure the rigid connection thereof to and the disconnection thereof from at least one part of a positioning trocar, and a second coupling means intended at least to ensure the rigid connection thereof to a removal trocar.

The guide pin of the invention can further include the following optional features, considered singly or according to any combinations technically possible:
  the guide rod of said pin is capable of being cut so that the end thereof is located beneath and in the vicinity of the skin surface when the pin is in the implanted position in the bone;
  at least one part of the head has a circular section with an average diameter D1, and the guide rod has a circular section with an average diameter D2 that is less than the diameter D1 of the head;
  the guide pin is made of stainless steel or titanium, and the diameter D2 of the guide rod is less than 2 millimetres;
  the head has a free end formed by a bevel, double bevel or diamond tip;
  the first coupling means comprises a threading produced on the guide rod;
  the threading is produced away from the head;
  the first coupling means further comprises a rotation locking element;
  the rotation locking element is produced at the head;
  the rotation locking element is in the vicinity of the rod;
  the locking element has a polygon-shaped section, for example a hexagonal section;
  the second coupling means is formed by a threading produced on the head;
  the threading is produced at the locking element;
  the locking element includes a smooth part and a threaded part also forming a second coupling means;
  the first and second coupling means are aligned.

The invention further relates to a trocar for placing an endosteal guide pin, which is essentially characterised in that it includes a first part comprising the guide pin, said pin including a head intended to be provisionally implanted in a bone, and a guide rod, coaxial with and rigidly connected to the head, ending in a free end, and adapted such that it is at least flush with the skin surface of the patient when the pin is in the implanted position in the bone, the positioning trocar further comprising a second hollow part to which the first part is coupled in a removable manner by means of a rigid connection system including a first coupling means provided on said pin and a cooperating coupling means provided on the positioning trocar, the guide rod of the guide pin being fitted inside the hollow part such that it slides, and in that the pin includes a second coupling means intended at least to ensure the rigid connection thereof to a removal trocar.

Advantageously, the free end of the hollow part includes driving means for driving the guide head into the bone, in particular rotating and, where appropriate, grasping means.

Preferably, the first coupling means of the removable rigid connection system includes a threading made away from the head of the guide pin, and in that the cooperating coupling means includes a tapping coincident with said threading.

More preferentially, the tapping is produced in a nut disposed coaxially to said hollow part of the positioning trocar, which nut cooperates with the threading such that the rotation of the nut drives the screwing or unscrewing of the guide rod of the pin relative to the rest of the positioning trocar in order to enable the guide pin to be rigidly connected to or disconnected from the second hollow part of the positioning trocar.

Preferentially, the tapping is located at the driving means of the positioning trocar.

Advantageously, the removable rigid connection system further includes a rotation locking element provided on the pin and a cooperating locking element provided in the hollow part of the trocar in order to prevent the rotation of the guide pin relative to the hollow part of the positioning trocar around the axis of said positioning trocar.

More preferentially, the rotation locking element is provided at the head of the pin.

Advantageously, the rotation locking element is located in the vicinity of the rod.

Preferably, the locking element has a polygon-shaped section, for example a hexagonal section, and in that the cooperating locking element is formed by a key made in the hollow part of the trocar and adapted for cooperating with the first locking element.

The invention further relates to a trocar for removing an endosteal guide pin for preparing a guide path for the implantation of a pedicle or orthopaedic screw, the pin including a head intended to be provisionally implanted in a bone, and a guide rod, coaxial with and rigidly connected to the head, ending in a free end adapted such that it is at least flush with the skin surface of the patient when the pin is in the implanted position in the bone, which pin includes a first coupling means intended to ensure the rigid connection thereof to and the disconnection thereof from at least one part of a positioning trocar, and a second coupling means intended at least to ensure the rigid connection thereof to a removal trocar, characterised in that it includes a hollow fixing rod intended to be fitted around the guide rod of said pin, and a coupling means cooperating with the second coupling means of said pin to form a removable rigid connection system enabling the guide pin to be removed when the second coupling means of the pin and the cooperating coupling means of the hollow rod of the removal trocar are assembled together.

Advantageously, the cooperating coupling means is formed by a tapping made on the inside face of the hollow rod, and which is capable of being assembled with the second coupling means of the guide pin formed by a threading made on the guide rod or on the end part of the head rigidly connected to the guide rod.

The invention further relates to a method for preparing a guide path for implanting a pedicle or orthopaedic screw, comprising the following steps of:

a. Inserting the positioning trocar described hereinabove;

b. Disconnecting and removing the second hollow part of the positioning trocar so as to only leave the pin implanted in the bone;

c. Cutting the free end of the rod of the pin such that the cut rod is located beneath and in the vicinity of the skin surface.

Preferentially, the method comprises an additional step of placing the removal trocar described hereinabove and of rigidly connecting same to the guide pin by the removable rigid connection system considered, followed by a step of removing the pin using the removal trocar.

Advantageously, the step of disconnecting the hollow part of the positioning trocar is carried out by unscrewing the nut from the threading of the free end of the rod, followed by the removal by translation along the axis of the rod of said hollow part.

Preferably, the placement of the removal trocar is carried out by screwing said trocar around the threading produced on the rod or on the head of the pin.

BRIEF DESCRIPTION OF THE FIGURES

Other characteristics and advantages of the invention will clearly emerge from the following description, which is given as a rough guide and in no way as a limited guide, with reference to the appended figures, from which:

FIGS. 5 to 12 show the operations for implanting in a vertebra and for removing the pin of the invention of the first alternative embodiment shown in FIG. 1, using the positioning trocar according to the first configuration shown in FIGS. 2 and 3, and the removal trocar according to the first configuration shown in FIG. 4.

DETAILED DESCRIPTION

The instrument of the invention firstly provides an endosteal guide pin having an unprecedented configuration which has a coaxial extension of the pin head capable of extending beneath and in the vicinity of the skin surface of the patient when the head is impacted in the bone. Thus, the operator can easily relocate the pin in order to place the pedicle screw.

The instrument of the invention further provides a positioning trocar which integrates said guide pin. More particularly, the positioning trocar comprises a first part formed by the guide pin and a second part including at least one hollow rod. The first part comprises a distal part of the positioning trocar formed by the head of the guide pin. The end of this distal part, and thus the free end of the head of the pin, can include a single bevel tip, or preferably a double bevel tip, which both enables single cutaneous passage when inserting the trocar and optimised impact of the pin in the bone. Alternatively, the free end of the head of the pin is a diamond tip, particularly suited for implanting the head of the pin with a positioning trocar associated with a powered driving system. The integration of the tip in the pin removes the need to use a fixing rod provided in the system of the prior art described hereinabove.

Figure 20:
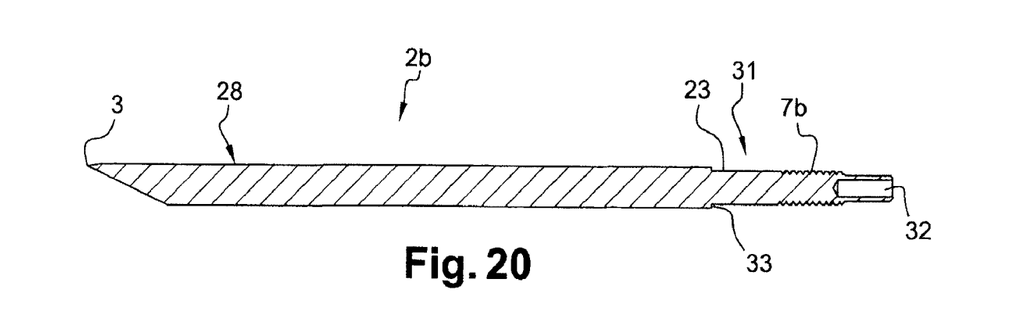
FIG. 20 is a longitudinal sectional view of the head of the guide pin in FIG. 17.
Figure 21:
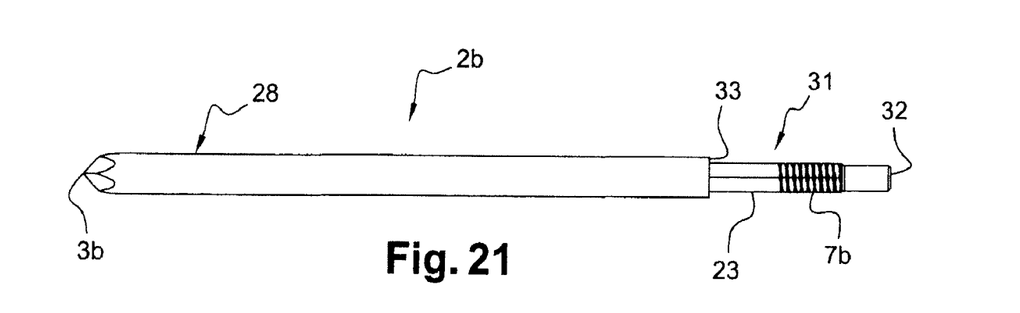
FIG. 21 is an overhead view of the head of the guide pin in FIG. 17.
Figure 22:
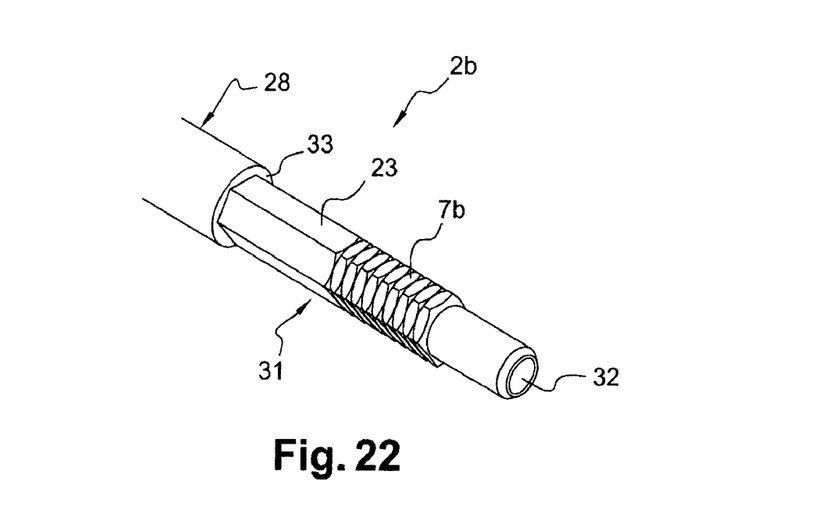
FIG. 22 is a perspective view of one part of the head of the guide pin in FIG. 17, in particular showing the junction portion with the guide rod, a hexagonal locking element and the second coupling means formed by a hexagonal threading.

Moreover, the pin and the rest of the trocar are rigidly connected by coupling means which can be, for the alternative embodiment shown in FIGS. 1 to 12, a bayonet rigid connection system. This system does not result in the mechanical strength issues of the thread pitch of the pin holder of the prior art, which allows the insertion of the positioning trocar and the implantation of the pin in the bone to be power-assisted. Other fixing means can be provided, for example a threading/tapping system and nut located in the vicinity of the free end of the second part or hollow part of the positioning trocar (FIGS. 14 to 16) with, where appropriate, locking means preventing any rotational movement of the guide pin along the axis thereof relative to the rest of the positioning trocar (FIGS. 20 to 22).

Finally, the instrument according to the invention further provides a trocar for removing the pin. According to one alternative embodiment, this removal trocar can be formed by the second part of the positioning trocar. In this scenario, the comprehensive instrument includes the second part of a positioning trocar also forming a removal trocar, and the guide pin forming a first part of the positioning trocar and the head whereof forms a distal part of the positioning trocar. The instrument is thus formed by only two parts.

The instrument of the invention allows the operations of placing the guide pin and of placing the pedicle screw to be separated. The guide pin can thus, for example, be placed by a first operator with image guidance, then the patient can be transported to another location. The operations of removing the guide pin and fixing the pedicle screw can be carried out by a second operator, in another location, for example in an operating room, without image guidance. Thus, in order to position the guide pin, image guidance devices that are not available in the operating room can be used. Moreover, the positioning of the pedicle screw is not subjected to restricted spatial requirements.

Figure 1:
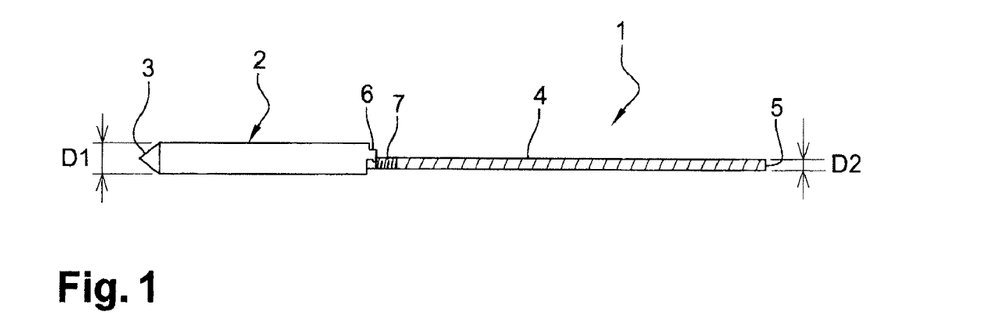
FIG. 1 is a diagrammatic side view of the guide pin of the invention according to a first alternative embodiment.

With reference to FIG. 1, the guide pin of the invention 1 includes a head 2 having a circular section with a diameter D1 and ending, at the free end thereof, in a double bevel tip 3 or a diamond tip. The pin 1 extends on the side opposite the tip 3 by a coaxial guide rod 4 having a circular section with a diameter D2 that is less than the diameter D1 of the head 2 and ending in a free end 5. The guide pin 1 thus extends longitudinally from the tip 3 of the head 2 to the free end 5 of the guide rod 4.

The end opposite the tip 3 of the head 2 includes a first coupling means formed by the male part 6 of a bayonet rigid connection system which is intended to cooperate with the female part of this system provided on the hollow part of the positioning trocar which will be described hereafter.

The guide rod 4 includes a second coupling means formed by a threading 7 intended to cooperate with a tapping provided on the removal trocar of the invention which will be described hereafter. Alternatively, as shown in FIGS. 17 to 22, the threading 7b intended to cooperate with the tapping of the removal trocar is produced on a part of the head 2b of the guide pin located in the vicinity of the guide rod 4b.

The guide pin is made of a metal material, for example of stainless steel or titanium. By way of illustration, the overall length of the pin is 150 millimetres, the diameter D1 is 2.4 millimetres and the diameter D2 is 1 millimetre. The length of the guide rod 4 is at least 100 millimetres in order to project from or at least lie flush with the skin surface when the head of the pin is in the implanted position in the bone (before any cutting operation is carried out on the guide rod).

Figure 2:
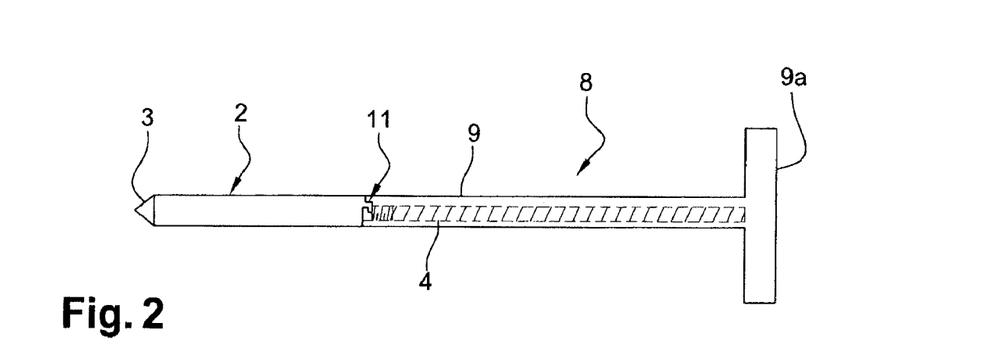
FIG. 2 is a diagrammatic side view of a guide pin positioning trocar of the invention according to a first configuration integrating, in the first part, said pin in FIG. 1, and shown when the pin is rigidly connected to the positioning trocar.
Figure 3:
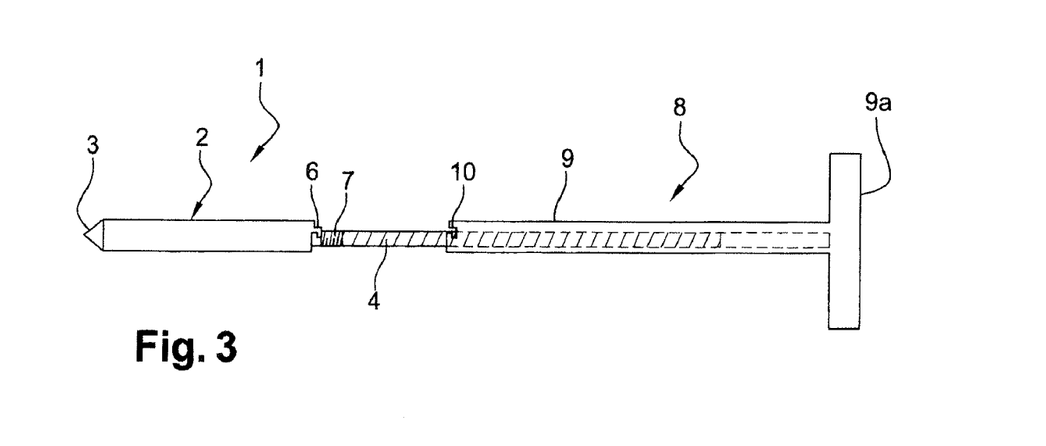
FIG. 3 is a diagrammatic side view of the guide pin positioning trocar of the invention in FIG. 2, shown when the pin is disassembled from the positioning trocar.
Figure 17:
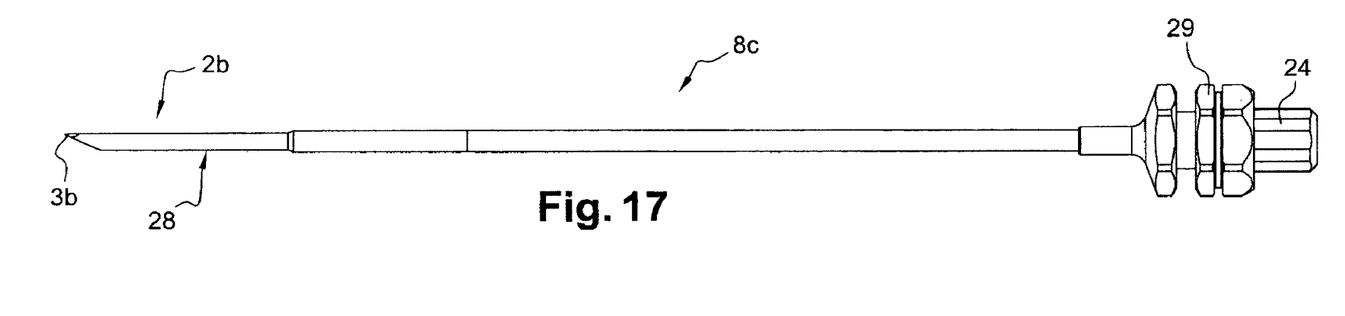
FIG. 17 is a diagrammatic side view of a guide pin positioning trocar of the invention according to a fourth configuration.
Figure 18:
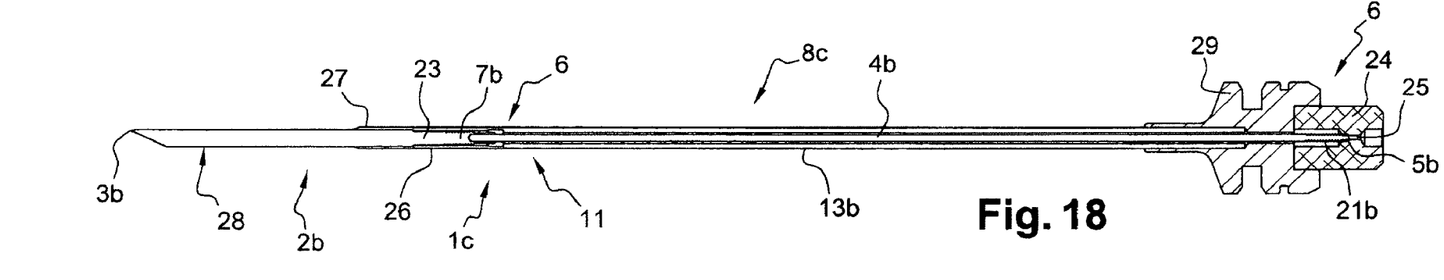
FIG. 18 is a longitudinal sectional view of the positioning trocar in FIG. 17.
Figure 19:
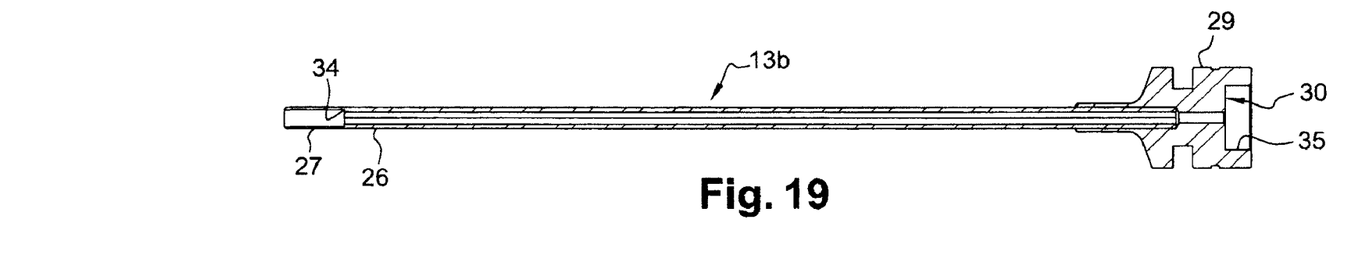
FIG. 19 is a longitudinal sectional view of a feature in FIG. 17, showing the hollow part of the positioning trocar.

With reference to FIGS. 2 and 3, the positioning trocar of the invention 8 includes a second so-called hollow part formed by a hollow rod 9 and ending in a grasping and driving handle 9a. This handle 9a allows the positioning trocar 8 to be manually inserted and removed. In place of this handle 9a, means for cooperating with a power tool can be provided for the power-assisted placement and removal of the trocar 8. Such means for cooperating with a power tool are shown in FIGS. 17 to 19, and are formed by a rotating member 29 rigidly connected to the free end of the hollow part of the positioning trocar 8c and intended to cooperate with the end piece forming a key of the power tool, for example a power screwdriver. In order to ensure the engagement of the rotating member 29 with the end piece of the screwdriver, said member 29 has a polygon-shaped section, preferentially a hexagonal section.

At the opposite end of the handle 9a, the hollow part 9 extends coaxially by a first part formed by the pin 1, the guide rod 4 whereof is fitted inside the hollow part 9 of the trocar 8 such that it slides.

Moreover and with reference to FIG. 3, the end of the hollow part 9 of the trocar 8 opposite the handle 9a has a female part 10 of a bayonet rigid connection system which cooperates with the male part 6 located at the end of the head 2 of the pin 1. The cooperation of these two parts 6, 10 forms (FIG. 2) the bayonet rigid connection system 11 enabling the hollow part 9 of the positioning trocar 8 to be rigidly connected to and disconnected, by rotation and longitudinal removal, from the pin 1.

Thus, the positioning trocar 8 integrates the guide pin 1 in FIG. 1 which is, via the bayonet rigid connection system 11, rigidly connected to or disconnected from the hollow part 9 of the trocar 8.

Figure 4:
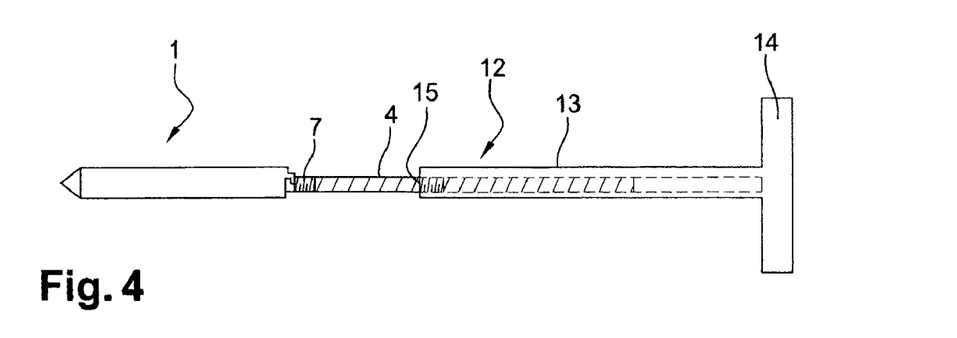
FIG. 4 is a diagrammatic side view of the removal trocar of the invention according to a first configuration, fitted around the guide rod of the pin of the invention in FIG. 1 and according to an intermediate disassembly position.

With reference to FIG. 4, the trocar for removing the pin 12 according to a first alternative embodiment is made of a hollow rod 13 ending, at one of the ends thereof, in a grasping handle 14. In place of this handle 14, means for cooperating with a power tool can be provided for the power-assisted placement and removal of the trocar 12, for example means identical to those described hereinabove relative to the hollow part of the positioning trocar.

At the opposite end of the handle 14, the internal circumference of the hollow tube 13 includes a tapping 15 which is capable of cooperating with the threading 7 provided on the guide rod 4 of the pin 1 and in the vicinity of the head 2 thereof. The internal diameter of the hollow tube 13 of the removal trocar 12 is thus adapted to the fitting of the removal trocar 12 around the guide rod 4 of the pin 1 and to the cooperation of the tapping 15 with the threading 7. The external diameter of the hollow tube is not subjected to any restrictions as regards the cooperation thereof with the pin 1. Alternatively, the removal trocar and the tapping thereof are adapted to cooperate with the threading 7b made on the head 2b of the guide pin, in the vicinity of the guide rod 4b (FIGS. 17 to 22).

Reference is made to FIGS. 5 to 12 to describe the different steps of placing the provisional pin 1 in the bone and of removing this pin, which are carried out by an operator or by two operators before implanting the pedicle or orthopaedic screw.

Figure 5:
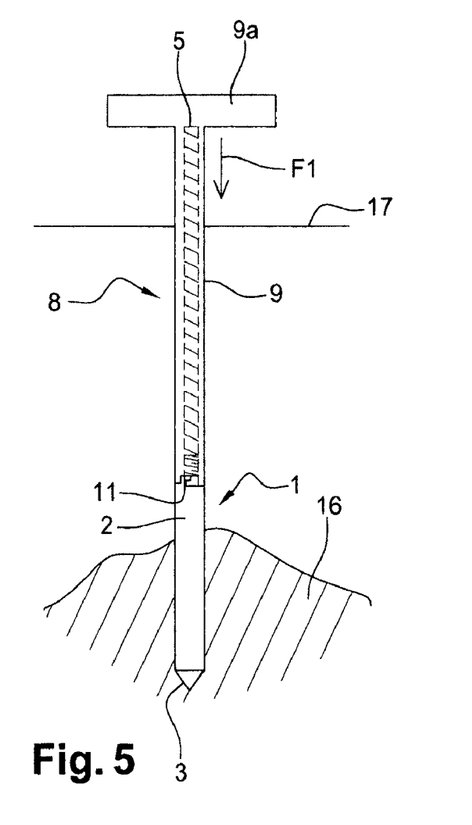
FIG. 5 is a diagrammatic view of a first step of placing the guide pin in a vertebra, in which step the first part of the positioning trocar formed by the head of the pin of the invention is implanted in the vertebra.

In FIG. 5, the positioning trocar 8 provided, at the end thereof, with the pin 1 is easily inserted according to the arrow F1 thanks to the double bevel tip 3. The pin is driven into the bone 16 manually or with power assistance, and the handle 10 of the positioning trocar 8 naturally projects from the skin surface 17, as well as the end 5 of the guide rod 4 of the pin 1.

Figure 6:
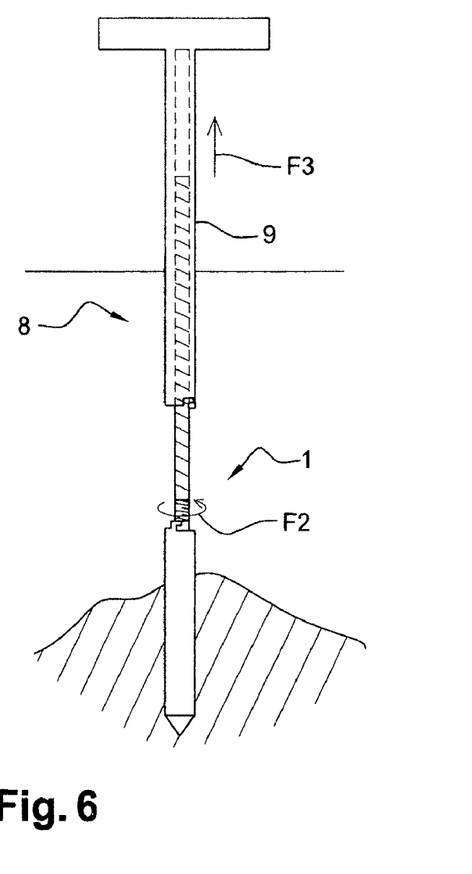
FIG. 6 is a diagrammatic view of a second step of placing the guide pin in a vertebra, in which step the hollow part of the positioning trocar has been disassembled from the guide pin and is extracted.

In FIG. 6, the removal of the hollow part 9 of the positioning trocar 8 is carried out by turning the handle 9a of the positioning trocar 8 in the anticlockwise direction according to the arrow F2 in order to disconnect the male and female parts of the bayonet rigid connection system 11 and disengage the pin 1 from the hollow part 9 of the positioning trocar 8, then by applying a tensile force according to the arrow F3.

Figure 7:
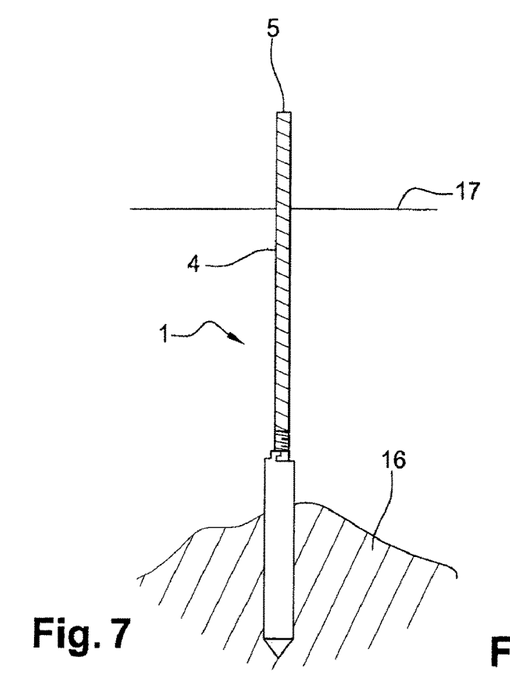
FIG. 7 is a diagrammatic view of the guide pin in place in the vertebra, the guide rod of the pin projecting from the skin surface.

As shown in FIG. 7, the pin 1 thus remains in place in the bone 16, the end 5 of the guide rod 4 projecting from the skin surface 17.

Figure 8:
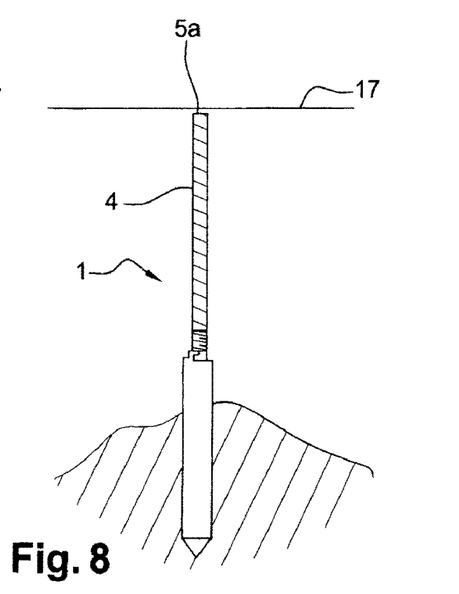
FIG. 8 is a diagrammatic view of a third step of placing the guide pin in a vertebra, wherein the guide rod of the pin is cut beneath and in the vicinity of the skin surface.

A suitable tool, for example surgical nippers, is then used to cut the end region of the guide rod 4 such that the new end 5a is located beneath and in the vicinity of the skin surface 17. This positioning on the one hand allows the operator or a second operator to relocate this end by simple palpation, and on the other hand prevents any risk of infection if the patient is transferred to a second location for the remaining operations.

All of these operations described with reference to FIGS. 5 to 8, and more particularly those of FIGS. 5 and 6, are preferably carried out with image, CT, X-ray or MRI guidance, by a radiologist. The position of the pin 1 in the bone is thus perfectly controlled.

Once the guide pin 1 is in position, the patient can be transported to a second location, which no longer requires any imaging device, for example an operating room. The operator can even be the same operator as the operator that fixed the guide pin, or another operator, for example a surgeon.

Figure 9:
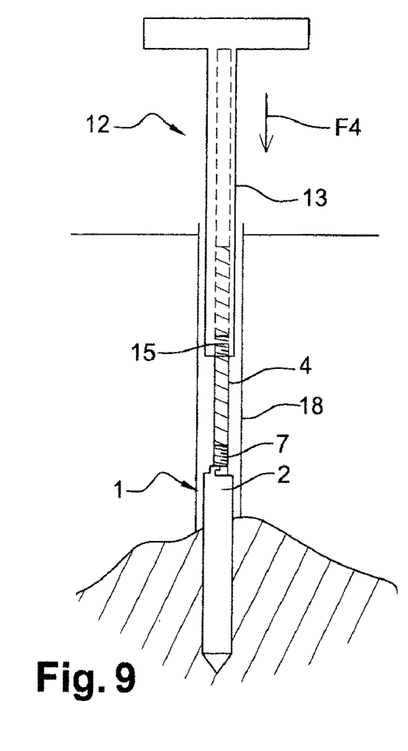
FIG. 9 is a diagrammatic view of a first step of removing the pin involving the prior placement of an external sheath and showing the insertion of a removal trocar according to the invention around the guide rod of the pin in position.

The placement of the pedicle screw by the operator begins by palpating the skin of the patient to locate the cut end 5a of the guide rod 4 of the pin 1. Once this end 5a has been located, the operator inserts an external sheath 18 around the guide pin 1.

The surgeon then inserts into the external sheath 18, around the guide rod 4 of the pin 1 and according to the arrow F4, the removal trocar 12 towards the head 2 of the pin 1.

Figure 10:
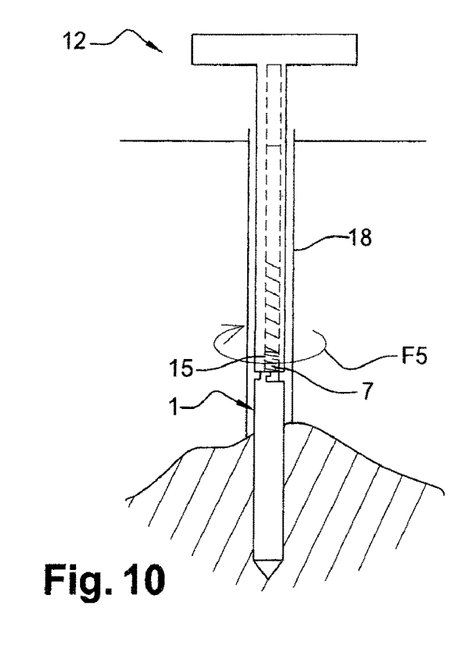
FIG. 10 is a diagrammatic view of a second step of removing the pin, in which step the removal trocar is rigidly connected to the pin.

With reference to FIG. 10, the removal trocar 12 is then rigidly connected to the pin by screwing in the clockwise direction according to the arrow F5 and by cooperation between the threading 7 on the guide rod 4 or the head 2 of the pin 1 and the tapping 15 on the inside face of the hollow tube 13 of the removal trocar 12.

Figure 11:
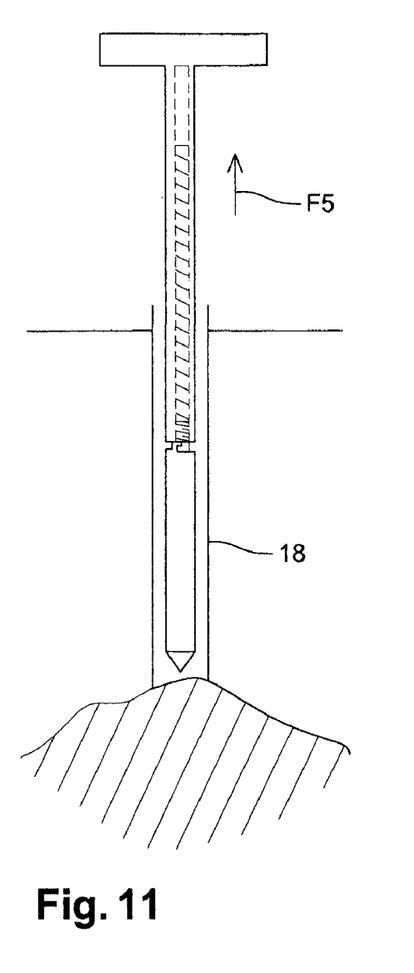
FIG. 11 is a diagrammatic view of a second step of removing the pin, in which step the removal trocar and the pin are extracted.
Figure 12:
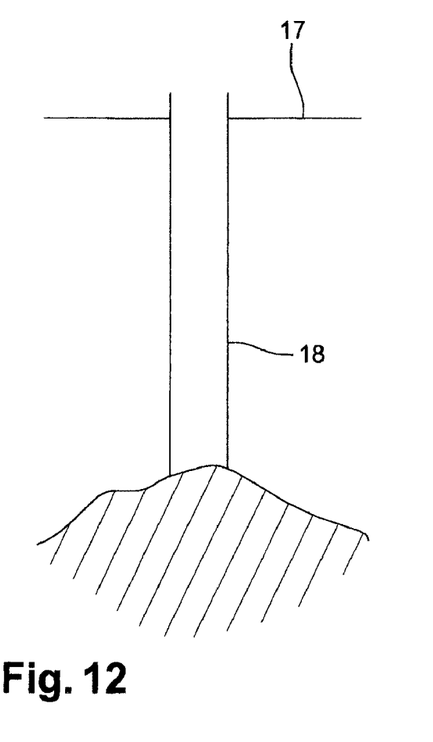
FIG. 12 is a diagrammatic view of the external sheath in position for guiding the operator for the placement of a pedicle screw.

With the removal trocar 12 and the guide pin 1 thus rigidly connected to one another, these two parts are extracted by manual or power-assisted grasping according to the arrow F5 (FIG. 11). Only the external sheath 18 then remains (FIG. 12), allowing the operator to insert and impact a new pin or a pedicle screw according to the trajectory of the guide pin.

Figure 13:
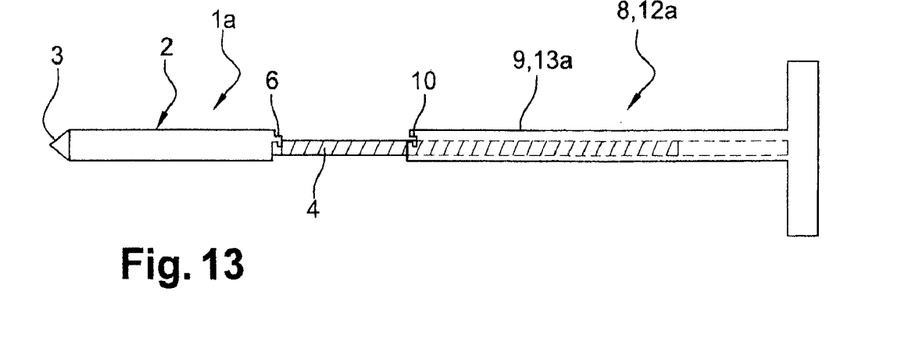
FIG. 13 is a diagrammatic view identical to that of FIG. 3 showing a trocar for positioning a guide pin according to one advantageous configuration wherein the hollow part of this positioning trocar forms a removal trocar.

FIG. 13 shows an advantageous alternative embodiment for producing the instrument of the invention, wherein the pin 1a is identical to the pin 1 in FIG. 4, with the exception that it does not include the threading 7. More specifically, in this alternative embodiment, the part (in this case the male part) of the bayonet rigid connection system forms both the first and second coupling elements. As a whole, and for all of the alternative embodiments of the invention, the first and second coupling means are aligned when the removal trocar is identical to the second part of the positioning trocar (8, 8b, 8c).

When the pin has this configuration, the hollow part 9 of the positioning trocar 8 (which is identical to that in FIGS. 2 and 3) thus forms a removal trocar 12a for which the hollow rod 13a does not include any tapping, the part 10 (in this case the female part) of the bayonet rigid connection system 11 allowing the rigid connection of the removal trocar 12a with the pin 1 for the extraction of this pin 1.

This configuration has the advantage of providing a comprehensive instrument that overcomes all of the aforementioned drawbacks using only two parts: the pin of the invention, and a trocar (removal trocar), otherwise referred to as the hollow part of the positioning trocar rigidly connected in a removable manner to said pin 1.

Figure 14:
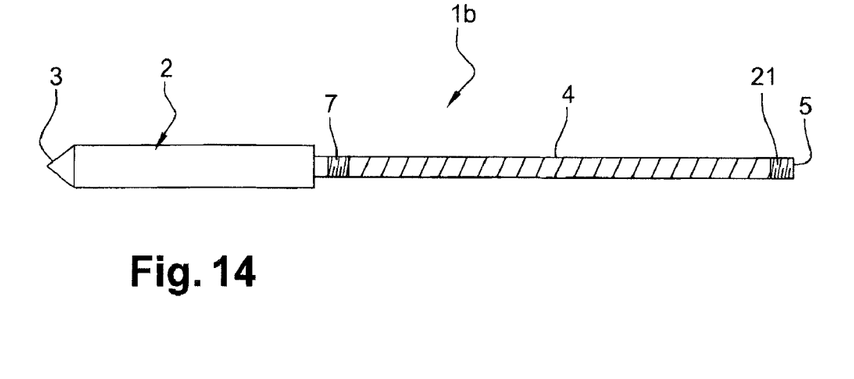
FIG. 14 is a diagrammatic side view of the guide pin of the invention according to a second alternative embodiment.
Figure 15:
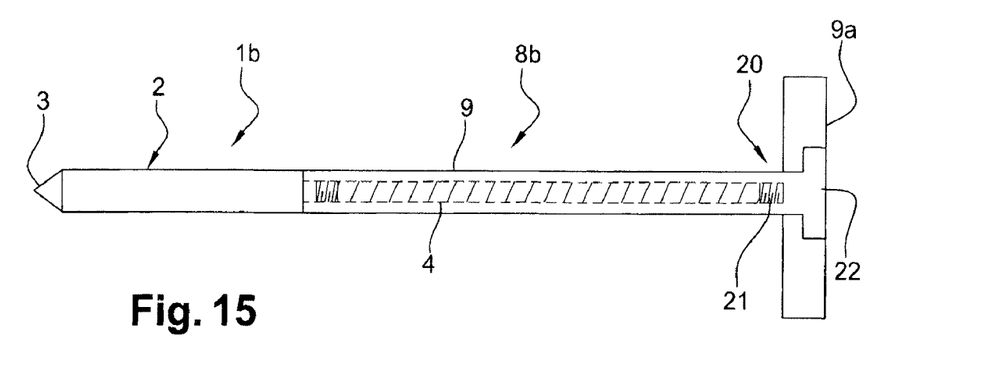
FIG. 15 is a diagrammatic side view of a guide pin positioning trocar of the invention according to a second configuration integrating, in the first part, the pin in FIG. 14, and shown when the pin is rigidly connected to the positioning trocar.
Figure 16:
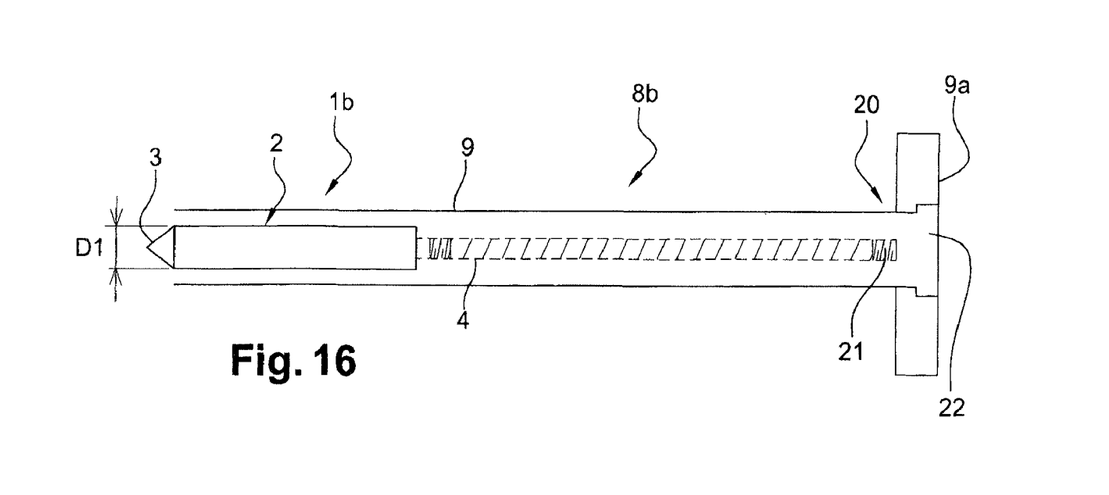
FIG. 16 is a diagrammatic side view of a guide pin positioning trocar of the invention according to a third configuration integrating, in the first part, the pin in FIG. 14, and shown when the pin is rigidly connected to the positioning trocar.

In an alternative embodiment shown in FIGS. 14 to 16, the removable rigid connection system 20 of the hollow part 9 of the positioning trocar 8b with the pin 1b includes a threading 21 located at the free end 5 of the guide rod 4 of the pin 1b which cooperates with a nut 22 located at the grasping handle 9a of the positioning trocar 8b via a tapping (not shown in the figures) made on the hollow inside face of the nut 22. Thus, the disconnection of the hollow part 9 from the pin 1b takes place by rotation of the nut 22, which prevents any risk, during this disconnection, of the head 2 of the pin 1b from rotating around itself when the patient suffers from a certain bone fragility.

Alternatively to this alternative embodiment shown in FIGS. 17 to 19, the tapped nut 24 forming a part of the positioning trocar 8c is disconnected from the hollow part of said positioning trocar 8c, or at least is entirely free to rotate relative to the hollow part, as will be described in more detail hereinbelow.

With reference to FIGS. 17 to 22, another embodiment of the guide pin 1c and of the positioning trocar 8c according to the invention will now be described.

Similarly to the embodiment of the positioning trocar 8 relative to FIGS. 2 and 3, the positioning trocar 8c relative to FIGS. 17 to 19 comprises the guide pin 1c and the hollow part 13b.

The head 2b of the guide pin 1c comprises, at the free end thereof, the tip 3b intended to penetrate the bone during implantation. This tip 3b comprises a double bevel machining easing the penetration of the head 2b into the bone. Alternatively, this tip 3b is a diamond tip. The head 2b comprises, at the opposite end thereof, a blind orifice 32 (see FIGS. 20 to 22), the section whereof is circular or polygonal for example, wherein the guide rod 4c is intended to be inserted and rigidly connected to said head 2b. In one possible alternative embodiment, the head 2b and the rod 4b are in one piece. The guide head 2b further comprises a portion 31, the section whereof is polygon-shaped, as well as a threading 7b forming a second coupling means with the removal trocar, which will be described hereinbelow.

The guide rod 4b of the pin 1c is threaded over a portion that is remote from the head of the pin. Given that this threading 21b is intended to cooperate with the tapped nut 24 which is a bolt 24 in this embodiment, it thus forms a first part of the coupling means 6 between the guide pin 1c and the hollow part 13b of the positioning trocar 8c. Preferentially, the length of the guide rod 4b is adapted such that the threading 21b is made at the free end 5b of said rod 4b. Nonetheless, the coaxial orifice of the bolt 24, wherein the tapping 25 intended to cooperate with the threading 21b of the first coupling means 6 is made, can be penetrating so as to allow said bolt 24 to be rigidly connected to a rod 4b, the length whereof is greater than the hollow part 13b of the positioning trocar.

Moreover, the portion 31 of the guide head 2b having a polygonal profile section, that is for example hexagonal, is preferentially remote from the tip 3b, the rest of the head 28 having a circular section. Moreover, the diameter of the portion having a circular section 28 is greater than the diameter of the portion having a polygonal section 31: a shoulder 33 is thus present at the junction between the portion having a circular section 28 and the portion having a polygonal section 31.

The portion having a polygonal section 31 made on the head 2b forms an element for locking the rotation of said head 2b relative to the hollow part 13b of the positioning trocar 8c, when this hollow part is engaged on the guide pin 1c. This locking element 31 forms the second part of the coupling means 6 of the guide pin 1c.

The locking element 31 of the guide pin 1c is intended to cooperate with a key 26 made in the hollow part 13b of the positioning trocar 8c, which, following the example of the positioning trocar 8 in FIGS. 2 and 3, comprises a hollow rod ending in grasping and driving means, these means being capable of being a handle or a rotating member 29 intended to cooperate with a power tool. Thus, the polygonal key 26 of the positioning trocar 8c is made at the end of the hollow part 13b of said trocar 8c opposite the grasping and driving means. The key 26 is itself extended by a cylindrical tube portion 27, the inside diameter whereof is greater than the inside diameter of the polygonal key 26. A shoulder 34 is thus present at the junction between the tube portion 27 and the polygonal key 26.

When the hollow part 13b of the positioning trocar 8c is fitted onto the guide rod 4b of the pin 1c such that it slides, the tube portion 27 of said hollow part 13b of the trocar engages around the portion having a circular section 28 of the head, and the polygonal key 26 engages around the element 31 for locking the rotation of the head 2b of the pin 1c, which enables any rotation of the pin 1c relative to the rest of the trocar 8c to be locked. Moreover, the two shoulders 33, 34 come to bear against and make contact with one another when the pin 1c and the rest of the positioning trocar 8c are in the correct position for the rigid connection thereof. The bolt 24 is thus screwed around the corresponding threading 21b of the guide rod 4b and forming part of the first coupling means 6 for rigidly securing the pin 1c to the hollow part 13b of the positioning trocar in order to form the positioning trocar 8c. The combined effect of the contact between the shoulders 33, 34, of the engagement of the key 26 around the polygonal portion 31 of the head 2b and the placement of the bolt 24 around the rod 4b completely locks the translation and rotation of the guide pin 1c relative to the rest of the positioning trocar. Thus, the removable rigid connection system of the positioning trocar 8c is formed by the threading 21b of the rod 4b, the hexagonal portion 31 of the head 2b, the key 26 and the tapping 25 of the bolt 24.

With reference to FIGS. 18 and 19, when the grasping and driving means are formed by the polygonal rotating member 29 intended to cooperate with a power tool, the bolt 24 is arranged such that it engages in a cylindrical recess 30 made in the wall of said rotating member 29, such that the bolt 24 is disposed coaxially to said rotating member 29 and thus to the hollow part 13b of the positioning trocar 8c. This bolt 24, which has a substantially cylindrical shape, can be entirely disconnected from the hollow part 13b of the positioning trocar 8c when it is not screwed onto the rod 4b. Alternatively, the bolt 24 can be mounted such that it rotates in the recess considered 30, for example using a flange (not shown) projecting from the cylindrical wall 35 of the recess 30 and cooperating with a groove (not shown) made in the cylindrical wall of the bolt 24. This specific arrangement prevents the loss of the bolt 24 and enables the pin 1c to be fixed to the hollow part 13b of the positioning trocar 8c without any rotation taking place between the pin 1c and the hollow part 13b of the trocar 8c.

Finally, the guide pin 1c comprises a threading 7b forming the second coupling means, intended to cooperate with the removal trocar.

This threading 7b can be made, as described hereinabove, on the rod 4b of the guide pin 1c. Advantageously, in the embodiment shown in FIGS. 17 to 22, the threading 7b is made on a portion of the head close to the rod 4b, and more preferentially on the portion having a polygonal section 31 such that this section 31 comprises the threading 7b and a hexagonal smooth part 23, as shown in particular in FIG. 22.

In this manner, the threading 7b has a dual purpose: that of forming the second coupling means of the guide pin 1c with the removal trocar, and that of ensuring, with the smooth part having a polygonal section 23, the locking of the rotation of the pin 1c relative to the rest of the positioning trocar 8c. The production of the threading 7b on the portion having a polygonal section 31 thus allows advantage to be taken of the length of said threading 7b in the overall length of the portion having a polygonal section 31, which ensures a particularly stable and effective engagement of the pin 1c with the hollow part 13b of the positioning trocar 8c, with the generation of maximum leverage when the practitioner exerts a rotational movement on the positioning trocar 8c in order to implant the guide head 2b in the bone.

According to another alternative embodiment shown in FIG. 16, the hollow part 9 of the positioning trocar 8b can extend longitudinally as far as the end 3 of the head 2 of the pin, while having a diameter that is greater than the diameter D1 of the head 2 of the pin 1b.

Similarly to the alternative embodiment shown in FIG. 13, the hollow part of the positioning trocar 8b can be provided such that it further forms a removal trocar, in which case the threading 7 of the pin 1b is not necessary. In this precise case, the guide head 2 does not comprise any portion having a polygonal section, since the sole trocar does not comprise any cooperating means capable of acting as a key.

The invention claimed is:

1. A trocar for positioning an endosteal guide pin, wherein it includes a first part comprising the guide pin, said pin including a head intended to be provisionally implanted in a bone, and a guide rod, coaxial with and rigidly connected to the head, ending in a free end, and adapted such that it is at least flush with the skin surface of the patient when the pin is in the implanted position in the bone, the positioning trocar further comprising a second hollow part to which the first part is coupled in a removable manner by means of a rigid connection system including a first coupling means provided on said pin and a cooperating coupling means provided on the positioning trocar, the guide rod of the guide pin being fitted inside the hollow part such that it slides, and the pin including a second coupling means intended at least to ensure the rigid connection thereof to a removal trocar, and wherein the removable rigid connection system further includes a rotation locking element provided on the head of the pin and a cooperating locking element provided in the hollow part of the trocar in order to prevent rotation of the guide pin relative to the hollow part of the positioning trocar around the axis of said positioning trocar.

2. The positioning trocar according to claim 1, wherein the free end of the hollow part includes driving means for driving the guide head into the bone, in particular rotating means and, where appropriate, grasping means.

3. The positioning trocar according to claim 1, wherein the first coupling means of the removable rigid connection system includes a threading made away from the head of the guide pin, and in that the cooperating coupling means includes a tapping coincident with said threading.

4. The positioning trocar according to claim 3, wherein the tapping is produced in a nut disposed coaxially to said hollow part of the positioning trocar, which nut cooperates with the threading such that the rotation of the nut drives the screwing or unscrewing of the guide rod of the pin relative to the rest of the positioning trocar in order to enable the guide pin to be rigidly connected to or disconnected from the second hollow part of the positioning trocar.

5. The positioning trocar according to claim 1, wherein the locking element has a polygon-shaped section, and in that the cooperating locking element is formed by a key made in the hollow part of the trocar and adapted for cooperating with the first locking element.

6. The positioning trocar according to claim 5, wherein the key is made on an inner surface of the hollow part, such that the key engages around the rotation locking element when the hollow part of the positioning trocar is fitted onto the guide rod of the pin.

7. The positioning trocar according to claim 5, wherein the key is a polygonal key extended by a cylindrical tube portion the inside diameter whereof is greater than the inside diameter of the key, such that a shoulder is present at the junction between the cylindrical tube portion and the polygonal key.

8. The positioning trocar according to claim 1, wherein the guide rod of the guide pin is capable of being cut so that the end thereof is located beneath and in the vicinity of the skin surface when the pin is in the implanted position in the bone.

9. The positioning trocar according to claim 1, wherein at least one part of the head has a circular section with an average diameter D1, and wherein the guide rod has a circular section with an average diameter D2 that is less than the diameter D1 of the head.

10. The positioning trocar according to claim 1, wherein the guide pin is made of stainless steel or titanium, and the diameter D2 of the guide rod is less than 2 millimeters.

11. The positioning trocar according to claim 1, wherein the head has a free end formed by a bevel, double bevel or diamond tip.

12. The positioning trocar according to claim 1, wherein the rotation locking element includes a smooth part and a threaded part also forming the second coupling means.

13. The positioning trocar according to claim 12, wherein the threaded part of the rotation locking element is made on a portion of the head close to the rod.

14. The positioning trocar according to claim 1, wherein a portion of the head has a polygonal profile section and the rest of the head has a circular section.

15. The positioning trocar according to claim 14, wherein a threading is made on the portion of the head having a polygonal section.

16. The positioning trocar according to claim 14, wherein the diameter of the portion of the head having a circular section is greater than the diameter of the portion of the head having a polygonal section, such that a shoulder is present at the junction between said two portions.

17. The positioning trocar according to claim 1, wherein the head comprises, at the opposite end of the free end, a blind orifice wherein the guide rod is intended to be inserted and rigidly connected to said head.

18. The positioning trocar according to claim 1, wherein the head and the guide rod are made in one piece.

* * * * *